United States Patent
Andrews et al.

(10) Patent No.: US 6,541,504 B1
(45) Date of Patent: Apr. 1, 2003

(54) (3Z)-3-(2,3-DIHYDRO-1H-INDEN-1-YLIDENE)-1,3-DIHYDRO-2H-INDOL-2-ONES AS KINASE INHIBITORS

(75) Inventors: Steven W. Andrews, Longmont, CO (US); Julie A. Wurster, Irvine, CA (US); Clarence E. Hull, III, Aliso Viejo, CA (US); Edward H. Wang, Dove Canyon, CA (US); Thomas Malone, Irvine, CA (US); Xialing Guo, Irvine, CA (US); Zhen Zhu, Tustin, CA (US)

(73) Assignee: Allergan Sales, LLC, Irvine, CA (US)

( * ) Notice: Subject to any disclaimer, the term of this patent is extended or adjusted under 35 U.S.C. 154(b) by 0 days.

(21) Appl. No.: 10/116,309

(22) Filed: Apr. 3, 2002

(51) Int. Cl.⁷ .................... A61K 31/404; C07D 407/04
(52) U.S. Cl. ........................ 514/414; 548/464
(58) Field of Search ............ 548/464; 514/414

(56) References Cited

U.S. PATENT DOCUMENTS

| | | | |
|---|---|---|---|
| 3,305,560 A | * | 2/1967 | Plostnieks |
| 3,941,807 A | * | 3/1976 | Borror |
| 4,966,849 A | | 10/1990 | Vallee et al. |
| 5,217,999 A | | 6/1993 | Levitzki et al |
| 5,302,606 A | | 4/1994 | Spada et al. |
| 5,330,992 A | | 7/1994 | Eissenstat et al. |
| 5,792,783 A | | 8/1998 | Tang et al. |
| 5,834,504 A | | 11/1998 | Tang et al. |
| 5,883,113 A | | 3/1999 | Tang et al. |
| 5,883,116 A | | 3/1999 | Tang et al. |
| 5,886,020 A | | 3/1999 | Tang et al. |

FOREIGN PATENT DOCUMENTS

| | | |
|---|---|---|
| WO | WO 91/15495 | 10/1991 |
| WO | WO 92/20642 | 11/1992 |
| WO | WO 92/21660 | 12/1992 |
| WO | WO 94/03427 | 2/1994 |
| WO | WO 94/10202 | 5/1994 |
| WO | WO 94/14808 | 7/1994 |

OTHER PUBLICATIONS

Plowman et al, "Receptor Tyrosine Kinases as Targets for Drug Intervention", 1994, DN&P 7(6): 334–339.

Bolen, "Nonreceptor tyrosine protein kinases", 1993, Oncogen 8: 2025–2031.

Kendall et al, "Inhibition of vascular endothelial cell growth factor activity by an endogenously encoded soluble receptor", 1994, Proc. Natl'l Acad. Sci 90: 10705–10709.

Kim et al, "Inhibition of vascular endothelial growth factor–induced angiogenesis suppresses tumor growth in vivo", Nature 362, 841–844, 1993.

Jellinek et al, "Inhibition of Receptor Binding by High–Affinity RNA Ligands to Vascular Endothelial Growth Factor", Biochemistry 33: 10450–10456, 1994.

Takano et al, "Inhibition of Angiogenesis by a Novel Diaminoanthraquinone that Inhibits Protein Kinase C.", 1993, Mol. Bio. Cell 4: 2072, p. 358A.

Kinsella et al, "Protein Kinase C Regulates Endothelial Cell Tube Formation on Basement Membrane Matrix, Matrigel", 1992, Experimental Cell Research, 199: 56–62.

Wright et al, "Inibition of Angiogenesis In Vitro and In Ovo With and Inhibitor of Cellular Protein Kinases, MDL 27032", 1992, Journal of Cellular Phys. 152: 448–457.

Mariani et al, "Inhibition of angiogenesis by FCE 26806, a potent tyrosine kinase inhibitor",1994, Proc. Am. Assoc. Cancer Res. 35:2268; p. 381.

\* cited by examiner

*Primary Examiner*—Joseph K. McKane
*Assistant Examiner*—Rebecca Anderson
(74) *Attorney, Agent, or Firm*—Robert J. Baran; Martin A. Voet; Carlos A. Fisher

(57) ABSTRACT

The present invention relates to organic molecules capable of modulating tyrosine kinase signal transduction in order to regulate, modulate and/or inhibit abnormal cell proliferation.

18 Claims, 1 Drawing Sheet

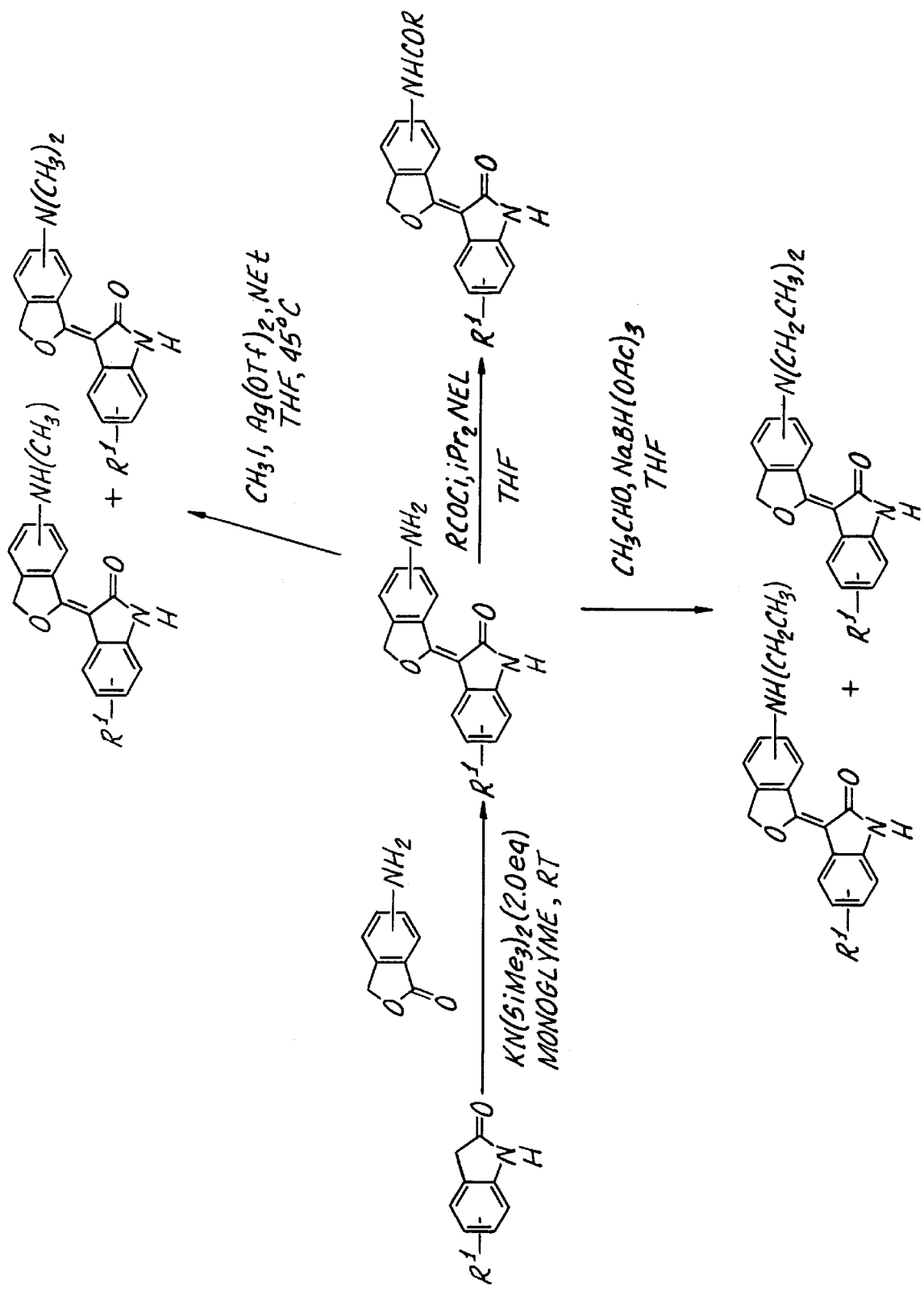

(3Z)-3-(2,3-DIHYDRO-1H-INDEN-1-YLIDENE)-1,3-DIHYDRO-2H-INDOL-2-ONES AS KINASE INHIBITORS

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKS) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phophorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-α, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fins-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334–339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025–2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (PCT Application No. WO 94/10202; Kendall & Thomas, 1994, Proc. Nat'l Acad. Sci 90: 10705–09; Kim, et al, 1993, Nature 362: 841–844), RNA ligands (Jellinek, et al, Biochemistry 33: 10450–56); Takano, et al, 1993, Mol. Bio.

Cell 4:358A; Kinsella, et al, 1992, Exp. Cell Res. 199: 56–62; Wright, et al, 1992, J. Cellular Phys. 152: 448–57) and tyrosine kinase inhibitors (PCT Application Nos. WO 94/03427; WO 92/21660; WO 91/15495; WO 94/14808; U.S. Pat. No. 5,330,992; Mariani, et al, 1994, Proc. Am. Assoc. Cancer Res. 35: 2268).

More recently, attempts have been made to identify small molecules which act as tyrosine kinase inhibitors. For example, bis monocyclic, bicyclic or heterocyclic aryl compounds (PCT Application No. WO 92/20642), vinylene-azaindole derivatives (PCT Application No. WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT Application No. WO 94/03427), tricyclic polyhydroxylic compounds (PCT Application No. WO 92/21660) and benzylphosphonic acid compounds (PCT Application No. WO 91/15495) have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

Finally, certain small compounds are disclosed in U.S. Pat. Nos. 5,792,783; 5,834,504; 5,883,113; 5,883,116 and 5,886,020 as useful for the treatment of diseases related to unregulated TKS transduction. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, restenosis, metabolic diseases such as diabetes, inflammatory diseases such as psoriasis and chronic obstructive pulmonary disease, vascular proliferative disorders such as diabetic retinopathy, age-related macular degeneration and retinopathy of prematurity, autoimmune diseases and transplant rejection.

In one illustrative embodiment, the compounds of the present invention have the formula:

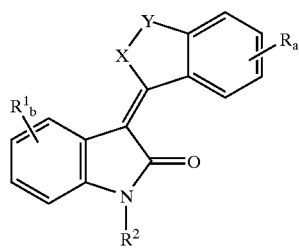

wherein

X is O;

Y is $[C(R^2)_2]_c$;

$R^1$ is selected from the group consisting of halogen, $C_1$ to $C_8$ alkyl, $CF_3$, $OCF_3$, $OCF_2H$, CN, $SR^2$, $(CH_2)_dC(O)OR^2$, $C(O)N(R^2)_2$, $(CH_2)_dOR^2$, $HNC(O)R^2$, HN—C(O)$OR^2$, $(CH_2)_dN(R^2)_2$, $SO_2N(R^2)_2$, $OP(O)(OR^2)_2$, $OC(O)OR^2$, $OCH_2O$, $N(R^2)(CH_2)_dN(R^2)_2$ and $O(CH_2)_dN(R^2)_2$;

$R^2$ is selected from the group consisting of hydrogen and $C_1$ to $C_8$ alkyl and phenyl;

R is selected from the group consisting of halogen, $C_1$ to $C_8$ alkyl, $CF_3$, $OCF_3$, $OCF_2H$, CN, $SR^2$, $(CH_2)_dC(O)OR^2$, $C(O)N(R^2)_2$, $(CH_2)_dOR^2$, $HNC(O)R^2$, HN—C(O)$OR^2$, $(CH_2)_dN(R^2)_2$, $SO_2N(R^2)_2$, $OP(O)(OR^2)_2$, $OC(O)OR^2$, $OCH_2O$;

b is 0 or an integer of from 1 to 2;

a is 0 or an integer of from 1 to 3;

c is an integer of from 1 to 2;

d is 0 or an integer of from 1 to 5 and further provided said alkyl or phenyl radicals may be substituted with one or two halo, hydroxy, lower alkyloxy, or lower alkyl amino radicals;

and pharmaceutically acceptable salts thereof.

BRIEF DESCRIPTION OF THE DRAWING FIGURES

The FIGURE shows a schematic of the preparation of the compounds of Examples 1 through 27.

DETAILED DESCRIPTION OF THE INVENTION

In one embodiment of the present invention $R^1$ is selected from the group consisting of H, i.e. b is 0; $CH_3$, F and Cl; preferably $R^1$ is H or $CH_3$.

Preferably, a is 0 or R is selected from the group consisting of $NHCOR^7$ and $N(R^7)_2$ wherein $R^7$ is selected from the group consisting of hydrogen, $C_1$ to $C_4$ alkyl and phenyl, wherein said alkyl or phenyl may be substituted with hydroxy, methylol or amino substituents and more preferably $R^7$ is selected from the group consisting of hydrogen, methyl, ethyl, hydroxypropyl, and aminomethylol phenyl.

Preferably $R^2$ is H.

Preferably c is 1.

In particular, the compounds of the present invention are selected from the compounds of Table 1, below.

TABLE 1

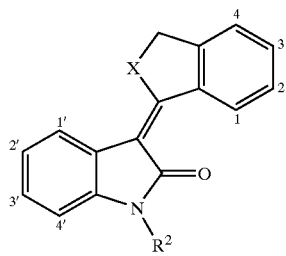

| Example Number | R² | 1 | 2 | 3 | 4 | 1' | 2' | 3' | 4' | X |
|---|---|---|---|---|---|---|---|---|---|---|
| Example 1 | H | H | H | H | H | H | H | H | H | O |
| Example 2 | H | H | H | H | H | H | Cl | H | H | O |
| Example 3 | H | H | H | H | H | CH₃ | H | H | H | O |
| Example 4 | H | H | H | H | H | H | F | H | H | O |
| Example 5 | H | H | NH₂ | H | H | H | H | H | H | O |
| Example 6 | H | H | NHCOCH₃ | H | H | H | H | H | H | O |
| Example 7 | H | H | NHCOCH₂CH₂CH₃ | H | H | H | H | H | H | O |
| Example 8 | H | H | NHCO-cyclopropyl | H | H | H | H | H | H | O |
| Example 9 | H | H | NHCOCH₂CH₂CH₂Cl | H | H | H | H | H | H | O |
| Example 10 | H | H | NHCOCH₂Ph-4-OCH₃ | H | H | H | H | H | H | O |
| Example 11 | H | H | NHCH₂CH₃ | H | H | H | H | H | H | O |
| Example 12 | H | H | H | NH₂ | H | H | H | H | H | O |
| Example 13 | H | H | H | NHCOPh-3-NH₂,6-CH₂OH | H | H | H | H | H | O |
| Example 14 | H | H | NHCH₂CH₂CH₂OH | H | H | H | H | H | H | O |
| Example 15 | H | H | H | NHCH₂CH₃ | H | H | H | H | H | O |
| Example 16 | H | H | NH₂ | H | H | H | Cl | H | H | O |
| Example 17 | H | H | H | NH₂ | H | H | Cl | H | H | O |
| Example 18 | H | H | H | NHCOCH₃ | H | H | H | H | H | O |
| Example 19 | H | H | H | NHCOCH₃ | H | H | Cl | H | H | O |
| Example 20 | H | H | NHCOCH₃ | H | H | H | Cl | H | H | O |
| Example 21 | H | H | N(CH₃)₂ | H | H | H | H | H | H | O |
| Example 22 | H | H | NHCH₃ | H | H | H | H | H | H | O |
| Example 23 | H | H | H | N(CH₃)₂ | H | H | H | H | H | O |
| Example 24 | H | H | H | NHCH₃ | H | H | H | H | H | O |
| Example 26 | H | H | NHCOCH₂CH₂Cl | H | H | H | H | H | H | O |
| Example 27 | H | H | N(CH₂CH₃)₂ | H | H | H | H | H | H | O |

The present invention is further directed to pharmaceutical compositions comprising a pharmaceutically effective amount of the above-described compounds and a pharmaceutically acceptable carrier or excipient. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

The following defined terms are used throughout this specification:

"Ac" refers to acetyl.

"Tf" refers to triflate.

"Me" refers to methyl.

"Et" refers to ethyl.

"tBu" refers to t-butyl.

"iPr" refers to I-propyl.

"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 7 carbons, most preferably 1 to 4 carbons. The alkenyl group may be optionally substituted with one or more substituents selected from the group consisting of hydroxyl, cyano, alkoxy, =O, =S, $NO_2$, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 7 carbons, most preferably 1 to 4 carbons. The alkynyl group may be optionally substituted with one or more substituents selected from the group consisting of hydroxyl, cyano, alkoxy, =O, =S, NO$_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, NO$_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a —N(R")R''' group, wherein R" and R''' are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R"", where R"" is aryl, C(CN)=C-aryl, CH$_2$CN, alkyaryl, sulfonamide, NH-alkyl, NH-alkylaryl, or NH-aryl.

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

Biological data for the compounds of the present invention was generated by use of the following assays.

VEGF Stimulated Ca$^{++}$ Signal in vitro

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 96-well fibronectin coated black-walled plates overnight @ 37° C./5%CO$_2$. Cells were loaded with calcium indicator Fluo-4 for 45 minutes at 37° C. Cells were washed 4 times (Original Cell Wash, Labsystems) to remove extracellular dye. For screening, cells were pre-incubated with test agents for 30 minutes at a single concentration (10 uM) or at concentrations ranging from 0.01 to 10.0 uM, followed by VEGF stimulation (5 ng/mL). Changes in fluorescence at 516 nm were measured simultaneously in all 96 wells using a cooled CCD camera. Data were generated by determining maxmin fluorescence levels for unstimulated, stimulated, and drug treated samples. IC$_{50}$ values for test compounds were calculated from % inhibition of VEGF stimulated responses in the absence of inhibitor.

Protocol for KDR Assay

The cytoplasmic domain of the human VEGF receptor (VEGFR-2) was expressed as a Histidine-tagged fusion protein following infection of insect cells using an engineered baculovirus. His-VEGFR-2 was purified to homogeneity, as determined by SDS-PAGE, using nickel resin chromatography. Kinase assays were performed in 96 well microtiter plates that were coated overnight with 30 µg of poly-Glu-Tyr (4:1) in 10 mM Phosphate Buffered Saline (PBS), pH 7.2–7.4. The plates were incubated with 1% BSA and then washed four times with PBS prior to starting the reaction. Reactions were carried out in 120 µL reaction volumes containing 3.6 µM ATP in kinase buffer (50 mM Hepes pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 0.5 ng of purified protein. Following a ten minute incubation at 25° C., the reactions were washed four times with PBS containing 0.05% Tween-20. 100 µl of a monoclonal anti-phosphotyrosine antibody-peroxidase conjugate was diluted 1:10000 in PBS-Tween-20 and added to the wells for 30 minutes. Following four washes with PBS-Tween-20, 100 µl of 0-Phenylenediamine Dihydrochloride in Phosphate-citrate buffer, containing urea hydrogen peroxide, was added to the wells for 7 minutes as a colorimetric substrate for the peroxidase. The reaction was terminated by the addition of 100 µl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

The results of said assays are set forth in Table 2, below.

TABLE 2

In vitro VEGF Inhibition

| Example Number | VEGF mean $IC_{50}$ (µM) (Cell based assay, $Ca^{++}$) | VEGF (% inhibition @ 10 uM) (Cell based assay, $Ca^{++}$) | VEGF mean $IC_{50}$ (µM) (Kinase assay, KDr with BSA) |
|---|---|---|---|
| Example 1 | 0.11 | 99 | |
| Example 2 | 0.05 | 98 | |
| Example 3 | 0.685 | 95 | |
| Example 4 | 0.055 | 99 | |
| Example 5 | 0.04 | 98 | 0.13 |
| Example 6 | 1.225 | 97 | 1.11 |
| Example 7 | | 5 | 9.78 |
| Example 8 | | 48 | 0.85 |
| Example 9 | | 35 | 0.13 |
| Example 10 | | 50 | 8.02 |
| Example 11 | 0.78 | 99 | 0.66 |
| Example 12 | 0.04 | 98 | 0.065 |
| Example 13 | 2.095 | 99 | |
| Example 14 | 0.85 | 100 | |
| Example 15 | | | |
| Example 16 | 0.01 | 99 | |
| Example 17 | 0.055 | 98 | |
| Example 18 | 0.04 | 97 | |
| Example 19 | 0.05 | 99 | |
| Example 20 | 0.215 | 99 | |
| Example 21 | | | |
| Example 22 | | | |
| Example 23 | | | |
| Example 24 | | | |
| Example 25 | | | |
| Example 26 | | | |
| Example 27 | | | |

As shown in Table 2, above, the compounds of Examples 1–6, 11–14 and 16–20 are preferred as they show % inhibition of VEGF>90% or VEGF $IC_{50}$<1.0 µM in either the cell or kinase assay.

EXAMPLES

Example 1

3-(3H-isobenzofuran-1-ylidene)-1,3-dihydro-indol-2-one

To a suspension of sodium hydride (6.0 g, 150 mmol, 60% in mineral oil) in 300 mL DMF was added oxindole (10.0 g, 75.1 mmol) in 50 mL DMF over 8 min. After stirring for 15 min at room temperature, a solution of phthalide (13.1 g, 97.6 mmol) in 50 mL DMF was added over 1 min. The mixture was stirred for 1.25 h, then poured into 1100 mL $H_2O$. Addition of 4% aqueous HCl solution gave a yellow solid which was filtered and rinsed with $H_2O$ to give the title compound (8.75 g, 47%).

Example 2

5-Chloro-3-(3H-isobenzofuran-1-ylidene)-1,3-dihydro-indol-2-one

To a solution containing 5-chlorooxindole (0.30 g, 1.79 mmol) and phthalide (0.312 g, 2.33 mmol) in 6.0 mL of dimethylformamide (DMF) was added 3.76 mL of sodium hexamethyldisilazane (1.0 M in tetrahydrofuran (THF)) over 1 min. The solution was stirred at room temperature for 25 min and then 85 mg (0.634 mmol) phthalide was added. After an additional 20 min at room temperature the mixture was poured into 70 mL of 4% aqueous HCl solution to give a yellow solid. The aqueous mixture was extracted with EtOAc and the organic phase washed with saturated $NaHCO_3$, brine and then dried with $Na_2SO_4$. After removal of the solvent in vacuo, the solid residue was recrystallized from MeOH/EtOAc to afford the title (141 mg, 28%) compound as a yellow solid.

Example 3

3-(3H-Isobenzofuran-1-ylidene)-4-methyl-1,3-dihydro-indol-2-one

To a solution containing 4-methyloxindole (0.15 g, 1.02 mmol) and phthalide (0.178 g, 1.33 mmol) in 3.0 mL DMF was added 2.14 mL of sodium hexamethyldisilazane (1.0 M in tetrahydrofuran (THF)) over 1 min. The solution was stirred at room temperature for 30 min and then poured into 50 mL of 4% HCl to give a yellow solid. The aqueous mixture was extracted with EtOAc and the organic phase washed with saturated $NaHCO_3$, $H_2O$, dilute HCl, brine and the solution dried with $Na_2SO_4$. The solvent was removed in vacuo and the solid obtained was purified by chromatography (silica gel, $CHCl_3$/EtOAc, 7:3). The solid obtained was recrystallized from EtOAc/hexanes to afford the title compounds (3.8 mg) as a yellow solid.

Example 4

5-Fluoro-3-(3H-isobenzofuran-1-ylidene)-1,3-dihydro-indol-2-one

To a solution at 0° C. containing 5-fluorooxindole (0.30 g, 1.99 mmol) and phthalide (0.400 g, 2.98 mmol) in 5.0 mL DMF was added 4.2 mL of sodium hexamethyldisilazane (1.0 M in THF) over 5 min. The solution was stirred at room temperature for 3 h and then quenched into cold 1.0 M aqueous HCl solution to give a yellow solid. The solid was collected and then purified by chromatography (silica gel, hexanes/EtOAc, 4:1) to afford the title compound (32 mg, 6%) as a yellow solid.

Example 5

3-(6Amino-3H-isobenzofuran-1-ylidene)-1,3-dihydro-indol-2-one

To a solution containing oxindole (0.5 g, 3.76 mmol) in 7.5 mL DMF was added 7.51 mL of sodium hexamethyldisilazane (1.0 M in THF) over 3 min. After stirring 10 min at room temperature, a solution of 6-aminophthalide (0.672 g, 4.51 mmol) in 4.0 mL DMF was added over 3 min. The reaction was stirred for 50 min at room temperature and then poured into 4% HCl to give a yellow solid. The solid was filtered to a wet cake and then partitioned between EtOAc and saturated $NaHCO_3$. Then the mixture was heated to dissolve the solid. The organic phase was washed with $H_2O$, brine and then dried with $Na_2SO_4$. The solvent was removed in vacuo and the resultant solid triturated with $CHCl_3$ to afford the title compound (445 mg, 45%) as a yellow solid.

Example 6

N-[3-(2-Oxo-1,2-dihydro-indol-3-ylidene)-1,3-dihydro-isobenzofuran-5-yl]-acetamide To a solution of 3-(6-Amino-3H-isobenzofuran-1-ylidene)-1,3-dihydro-indol-2-one (50.0 mg, 0.189 mmol) and N,N-diisopropylethylamine (98.8 µL, 0.567 mmol) in 2.0 mL THF was added acetyl chloride (13.4 µL, 0.189 mmol). After stirring a troom temperature for 1 h, the slurry was partitioned between $NaHCO_3$ solution and EtOAc (warmed to dissolve solid). The organic phase was washed with $H_2O$, 4% aqueout HCl solution, $H_2O$, saturated $NaHCO_3$, brine and dried with $Na_2SO_4$. After concentrating in vacuo the residue was triturated with EtOAc to give the title compound (47.4 mg, 82%) as a yellow solid.

Example 7

N-[3-(2-Oxo-1,2-dihydro-indol-3-ylidene)-1,3-dihydro-isobenzofuran-5-yl]-butyramide To a solution of 3-(6-Amino-3H-isobenzofuran-1-ylidene)-1,3-dihydro-indol-2-one (50.0 mg, 0.189 mmol) and N,N-diisopropylethylamine (98.8 µL, 0.567 mmol) in 2.0 mL THF was added butyryl chloride (19.6 µL, 0.189 mmol). After stirring at room temperature for 1 h, the slurry was filtered and rinsed with MeOH and EtOAc/hexanes (1:1) to afford the title compound (46.2 mg, 73%) as a yellow solid.

Example 8

Cyclopropanecarboxylic acid [3-(2-oxo-1,2-dihydro-indol-3-ylidene)-1,3-dihydro-isobenzofuran-5-yl]-amide To a solution of 3-(6-Amino-3H-isobenzofuran-1-ylidene)-1,3-dihydro-indol-2-one (50.0 mg, 0.189 mmol) and N,N-diisopropylethylamine (98.8 µL, 0.567 mmol) in 2.0 mL THF was added cyclopropane carbonyl chloride (17.2 µL, 0.189 mmol). After stirring at room temperature for 1 h, the slurry was warmed briefly, stirred 10 min at room temperature, filtered and rinsed with MeOH and EtOAc/hexanes (1:1) to afford the title compound (44.7 mg, 71%) as a yellow solid.

Example 9

4-Chloro-N-[3-(2-oxo-1,2-dihydro-indol-3-ylidene)-1,3-dihydro-isobenzofuran-5-yl]-butyramide To a solution of 3-(6-Amino-3H-isobenzofuran-1-ylidene)-1,3-dihydro-indol-2-one (50.0 mg, 0.189 mmol) and N,N-diisopropylethylamine (98.8 µL, 0.567 mmol) in 2.0 mL THF was added 4-chlorobutyryl chloride (21.2 µL, 0.189 mmol). After stirring at room temperature for 1 h, the slurry was filtered and rinsed with MeOH and EtOAc/hexanes (1:1) to afford the title compound (58.8 mg, 84%) as a yellow solid.

Example 10

2-(4-Methoxy-phenyl)-N-[3-(2-oxo-1,2-dihydro-indol-3-ylidene)-1,3-dihydro-isobenzofuran-5-yl]-acetamide To a solution of 3-(6-Amino-3H-isobenzofuran-1-ylidene)-1,3-dihydro-indol-2-one (50.0 mg, 0.189 mmol) and N,N-diisopropylethylamine (98.8 µL, 0.567 mmol) in 2.0 mL THF was added 4-methoxyphenylacetyl chloride (28.9 µL, 0.189 mmol). After stirring at room temperature for 1 h, the slurry was warmed briefly, stirred 10 min at room temperature, filtered and rinsed with MeOH and EtOAc/hexanes (1:1) to afford the title compound (48.3 mg, 62%) as a yellow solid.

Example 11

3-(6Ethylamino-3H-isobenzofuran-1-ylidene)-1,3-dihydro-indol-2-one

A mixture of 3-(6-Amino-3H-isobenzofuran-1-ylidene)-1,3-dihydro-indol-2-one (50.0 mg, 0.189 mmol), acetaldehyde (10.0 mg, 0.227 mmol), and sodium triacetoxyborohydride (52.1 mg, 0.246 mmol) was stirred at room temperature for 2.5 h. The reaction was then partitioned between EtOAc and $H_2O$. The organic phase was washed with $H_2O$, brine and then dried with $Na_2SO_4$. The solvent was removed in vacuo and the residue recrystallized from EtOAc/hexanes to afford the title compound (21.6 mg, 39%) as a yellow solid.

Example 12

3-(5-Amino-3H-isobenzofuran-1-ylidene)-1,3-dihydro-indol-2-one

To a solution containing oxindole (0.5 g, 3.76 mmol) in 7.5 mL DMF was added 7.51 mL of sodium hexamethyldisilazane (1.0 M in THF) over 3 min. After stirring 10 min at room temperature, a solution of 5-aminophthalide (0.672 g, 4.51 mmol) in 4.0 mL DMF was added over 3 min. The reaction was stirred for 30 min at room temperature and then poured into 4% aqueous HCl solution to give a yellow cloudy solution. After stirring the mixture 3 min, the solution was made basic by adding saturated $NaHCO_3$. The yellow solid was filtered, washed with $H_2O$, and then dissolved in $CHCl_3$/MeOH. The solvent was removed in vacuo and the solid purified by chromatography (silica gel, $CHCl_3$/MeOH, 95:5) to give the title compound (345 mg, 35%) as a yellow solid.

Example 13

5-Amino-2-hydroxymethyl-N-[3-(2-oxo-1,2-dihydro-indol-3-ylidene)-1,3-dihydro-isobenzofuran-5-yl]-benzamide To a solution containing oxindole (1.5 g, 11.3 mmol) in 23 mL DMF was added 22.54 mL of sodium hexamethyldisilazane (1.0 M in THF) over 5 min. After stirring 5 min at rt, a solution of 6-aminophthalide (2.017 g, 13.5 mmol) in 11.0 mL DMF was added over 4 min. The reaction was stirred for 30 min at room temperature and then quenched into 4% aqueous HCl solution. The aqueous solution was neutralized to pH 6 with 1 M NaOH and then made basic with saturated NaHCO$_3$. The solid was filtered and washed with H$_2$O and then partitioned between EtOAc and saturated NaHCO$_3$ (heated to dissolve the solid). The organic phase was washed with H$_2$O, brine and then dried with Na$_2$SO$_4$. The solvent was removed in vacuo and the solid triturated with CHCl$_3$. The yellow solid was filtered (1.2 g) and the filtrate concentrated in vacuo. The solid (0.88 g) obtained from the filtrate was purified by chromatography (CHCl$_3$/MeOH, 96:4) to afford the lower R$_f$ product, which after trituration with CHCl$_3$, gave the title compound (7.6 mg) as a yellow solid.

Example 14

3-[6-(3-Hydroxy-propylamino)-3H-isobenzofuran-1-ylidene]-1,3-dihydro-indol-2-one A mixture of 3-(6-Amino-3H-isobenzofuran-1-ylidene)-1,3-dihydro-indol-2-one (25.0 mg, 0.095 mmol), 3-bromo-1-propanol (85.5 µL, 0.946 mmol), and silver sulfate (59.0 mg, 0.189 mmol) in 0.8 mL DMF was heated at 120° C. for 1.5 h. The mixture was partitioned between EtOAc and H$_2$O and the organic layer separated from the silver salts. The solution was washed with H$_2$O, brine and then dried with Na$_2$SO$_4$. Concentrating the solution in vacuo gave a residue which was purified by chromatography (silica gel, CHCl$_3$/MeOH, 96:4) to give the title compound (3 mg, 10%) as a yellow solid.

Example 15

3-(5-Ethylamino-3H-isobenzofuran-1-ylidene)-1,3-dihydro-indol-2-one

A mixture of 3-(5-Amino-3H-isobenzofuran-1-ylidene)-1,3-dihydro-indol-2-one (50.0 mg, 0.189 mmol), acetaldehyde (10.0 mg, 0.227 mmol), and sodium triacetoxyborohydride (52.1 mg, 0.246 mmol) was stirred at room temperature for 50.5 h. The reaction was then partitioned between EtOAc and H$_2$O. The organic phase was washed with H$_2$O, brine and then dried with Na$_2$SO$_4$. The solvent was removed in vacuo and the solid chromatographed (CHCl$_3$/MeOH, 97.5:2.5) to afford the title compound (14.1 mg, 25%) as a yellow solid.

Example 16

3-(6-Amino-3H-isobenzofuran-1-ylidene)-5-chloro-1,3-dihydro-indol-2-one

To a solution of 5-chlorooxindole (0.629 g, 3.78 mmol) in 10.0 mL monoglyme was added 7.51 mL sodium hexamethyldisilazane (1.0 M in THF) over 3 min. After stirring at room temperature for 8 min, a slurry of 6-aminophthalide (0.561 g, 3.78 mmol) in 4.0 mL of monoglyme was added in one portion. The mixture was stirred for 40 min and then quenched into 100 mL of 4% aqueous HCl solution. The yellow solid was filtered and then partitioned between EtOAc and saturated NaHCO$_3$ (heated to dissolve the solid). The organic phase was washed with H$_2$O, brine and then dried with Na$_2$SO$_4$. The solvent was removed in vacuo and the residue was triturated with MeOH to give the title compound (439 mg, 39%) as a yellow solid.

Example 17

3-(5-Amino-3H-isobenzofuran-1-ylidene)-5-chloro-1,3-dihydro-indol-2-one

To a solution of 5-chlorooxindole (0.629 g, 3.78 mmol) in 10.0 mL monoglyme was added 7.51 mL sodium hexamethyldisilazane (1.0 M in THF) over 3 min. After stirring a troom temperature for 8 min, a solution of 5-aminophthalide (0.561 g, 3.78 mmol) in 3.0 mL of DMF was added over 1 min. The mixture was stirred for 40 min and then quenched into 4% aqueous HCl solution. The aqueous solution was neutralized to pH 7 with 1 M NaOH and then made basic with saturated NaHCO$_3$. The solid was filtered and washed with H$_2$O and then partitioned between EtOAc and saturated NaHCO$_3$ (heated to dissolve the solid). The organic phase was washed with H$_2$O, brine and then dried with Na$_2$SO$_4$. The solvent was removed in vacuo and the residue triturated with MeOH to give the title compound (353 mg, 31%) as a yellow solid.

Example 18

N-[1-(2-Oxo-1,2-dihydro-indol-3-ylidene)-1,3-dihydro-isobenzofuran-5-yl]-acetamide To a solution of 3-(5-Amino-3H-isobenzofuran-1-ylidene)-1,3-dihydro-indol-2-one (50.0 mg, 0.189 mmol) and N,N-diisopropylethylamine (98.8 µL, 0.567 mmol) in 2.0 mL THF was added acetyl chloride (13.4 µL, 0.189 mmol). After stirring at room temperature for 3 h, the mixture was concentrated in vacuo and the solid triturated with MeOH. Filtering the mixture and rinsing with MeOH and hexanes/EtOAc (7:3) afforded the title compound (42.2 mg, 73%) as a yellow solid.

Example 19

N-[1-(5-Chloro-2-oxo-1,2-dihydro-indol-3-ylidene)-1,3-dihydro-isobenzofuran-5-yl]-acetamide To a solution of 3-(5-Amino-3H-isobenzofuran-1-ylidene)-5-chloro-1,3-dihydro-indol-2-one (56.5 mg, 0.189 mmol) and N,N-diisopropylethylamine (98.8 µL, 0.567 mmol) in 2.5 mL THF was added acetyl chloride (13.4 µL, 0.189 mmol). After stirring at room temperature for 3 h, the mixture was concentrated in vacuo and the solid triturated with MeOH. Filtering the mixture and rinsing with MeOH and hexanes/EtOAc (7:3) afforded the title compound (55.9 mg, 87%) as a yellow solid.

Example 20

N-[3-(5-Chloro-2-oxo-1,2-dihydro-indol-3-ylidene)-1,3-dihydro-isobenzofuran-5-yl]-acetamide To a solution of 3-(6-Amino-3H-isobenzofuran-1-ylidene)-5-chloro-1,3-dihydro-indol-2-one (56.5 mg, 0.189 mmol) and N,N-diisopropylethylamine (98.8 µL, 0.567 mmol) in 2.5 mL THF was added acetyl chloride (13.4 µL, 0.189 mmol). After stirring at room temperature for 3 h, the mixture was filtered and rinsed with isopropanol and hexanes/EtOAc (7:3) to give the title compound (46.9 mg, 73%) as a yellow solid.

Example 21 and Example 22

3-(6-Dimethylamino-3H-isobenzofuran-1-ylidene)-1,3-dihydro-indol-2-one and 3-(6-Methylamino-3H-isobenzofuran-1-ylidene)-1,3-dihydro-indol-2-one To a solution of 3-(6-Amino-3H-isobenzofuran-1-ylidene)-1,3-dihydro-indol-2-one (50.0 mg, 0.189 mmol) and N,N-diisopropylethylamine (65.8 µL, 0.378 mmol) in 2.0 mL THF was added iodomethane (12.9 µL, 0.208 mmol). After stirring at room temperature for 21 h, silver triflate (53.4 mg, 0.208 mmol) was added and the mixture heated at 45° C. for 16 h. The mixture was partitioned between EtOAc and saturated NaHCO$_3$ and the organic separated. The organic layer was washed with H$_2$O, brine and then dried with Na$_2$SO$_4$. The solution was evaporated in vacuo and the residue purified by chromatography (silica gel, 2% MeOH/CHCl$_3$) to give 3-(6-Dimethylamino-3H-isobenzofuran-1-ylidene)-1,3-dihydro-indol-2-one (3.6 mg) as a yellow solid and 3-(6-Methylamino-3H-isobenzofuran-1-ylidene)-1,3-dihydro-indol-2-one (6.3 mg) as a yellow solid.

Example 23 and Example 24

3-(5-Dimethylamino-3H-isobenzofuran-1-ylidene)-1,3-dihydro-indol-2-one and 3-(5-Methylamino-3H-isobenzofuran-1-ylidene)-1,3-dihydro-indol-2-one To a solution of 3-(5-Amino-3H-isobenzofuran-1-ylidene)-1,3-dihydro-indol-2-one (50.0 mg, 0.189 mmol) and N,N-diisopropylethylamine (65.8 μL, 0.378 mmol) in 2.0 mL THF was added iodomethane (12.9 μL, 0.208 mmol). After stirring at room temperature for 21 h, silver triflate (53.4 mg, 0.208 mmol) was added and the mixture heated at 45° C. for 16 h. The mixture was partitioned between EtOAc and saturated NaHCO$_3$ and the organic separated. The organic layer was washed with H$_2$O, brine and then dried with Na$_2$SO$_4$. The solution was evaporated in vacuo and chromatographed with 2% MeOH/CHCl$_3$ to give 3-(5-Dimethylamino-3H-isobenzofuran-1-ylidene)-1,3-dihydro-indol-2-one (1.2 mg) as a yellow-orange solid and 3-(5-Methylamino-3H-isobenzofuran-1-ylidene)-1,3-dihydro-indol-2-one (8.9 mg) as an orange solid.

Example 26

4-Chloro-N-[3-(2-oxo-1,2-dihydro-indol-3-ylidene)-1,3-dihydro-isobenzofuran-5-yl]-propionamide To a solution of 3-(6-Amino-3H-isobenzofuran-1-ylidene)-1,3-dihydro-indol-2-one (50.0 mg, 0.189 mmol) and N,N-diisopropylethylamine (98.8 μL, 0.567 mmol) in 2.0 mL THF was added 3-chloropropionyl chloride (21.2 μL, 0.189 mmol). After stirring at room temperature for 1 h, the slurry was filtered and rinsed with MeOH and EtOAc/hexanes (1:1) to afford the title compound (58.8 mg, 84%) as a yellow solid.

Example 11 and Example 27

3-(6-Ethylamino-3H-isobenzofuran-1-ylidene)-1,3-dihydro-indol-2-one and 3-(6-Diethylamino-3H-isobenzofuran-1-ylidene)-1,3-dihydro-indol-2-one A mixture of 3-(6-Amino-3H-isobenzofuran-1-ylidene)-1,3-dihydro-indol-2-one (581 mg, 2.20 mmol), acetaldehyde (116 mg, 2.64 mmol), and sodium triacetoxyborohydride (606 mg, 2.86 mmol) was stirred at room temperature for 3 h. The reaction was then partitioned between ethyl acetate and H$_2$O. The organic phase was washed with dilute aqueous NaHCO$_3$ solution, H$_2$O, brine and then dried with Na$_2$SO$_4$. The solvent was removed in vacuo and the residue was dissolved in CHCl$_3$/MeOH and purified by chromatography (silica gel, hexanes/EtOAc, 7:3) to give 3-(6-Ethylamino-3H-isobenzofuran-1-ylidene)-1,3-dihydro-indol-2-one (395.1 mg, 61%) as a yellow solid and 3-(6-Diethylamino-3H-isobenzofuran-1-ylidene)-1,3-dihydro-indol-2-one (32.9 mg, 5%) as a yellow solid.

The present invention is not to be limited in scope by the exemplified embodiments which are intended as illustrations of single aspects of the invention only. Indeed, various modifications of the invention in addition to those described herein will become apparent to those skilled in the art from the foregoing description. For example novel compounds of formula II, below may be utilized in the method of treating diseases described above.

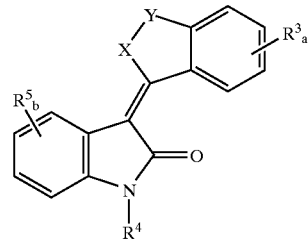

wherein X is O; Y is [C(R$^4$)$_2$]$_c$; R$^5$ is selected from the group consisting of halogen, nitro, hydroxy, hydrocarbyl, substituted hydrocarbyl, amide, thioamide, amine, thioether and sulfonyl; R$^3$ is selected from the group consisting of halogen, nitro, hydroxy, hydrocarbyl, substituted hydrocarbyl, amide, thioamide, amine, thioether and sulfonyl and phosphonic acid; R$^4$ is selected from the group consisting of hydrogen, hydrocarbyl and substituted hydrocarbyl; c is an integer of from 1 to 2; b is 0 or an integer from 1 to 2; a is 0 or an integer of from 1 to 3 and pharmaceutically acceptable salts thereof. Said hydrocarbyl and/or substituted hydrocarbyl may be alkyl, alkenyl, alkynyl, aryl (including carbocylic aryl and heterocyclic aryl) and alkaryl.

Such modifications are intended to fall within the scope of the appended claims.

All references cited herein are hereby incorporated by reference in their entirety.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed:

1. A compound represented by the general formula I

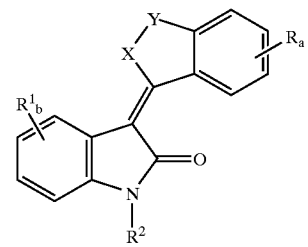

wherein
X is O;
Y is [C(R$^2$)$_2$]$_c$;
R$^1$ is selected from the group consisting of halogen, C$_1$ to C$_8$ alkyl, CF$_3$, OCF$_3$, OCF$_2$H, CN, SR$^2$, (CH$_2$)$_d$C(O)OR$^2$, C(O)N(R$^2$)$_2$, (CH$_2$)$_d$OR$^2$, HNC(O)R$^2$, HN—C (O)OR², (CH₂)$_d$N(R²)₂, SO₂N(R²)₂, OP(O)(OR²)₂, OC(O)OR², OCH₂O, N(R²)(CH₂)$_d$N(R²)₂ and O(CH₂)$_d$N(R²)₂;

R² is selected from the group consisting of hydrogen and C₁ to C₈ alkyl and phenyl;

R is selected from the group consisting of halogen, C₁ to C₈ alkyl, CF₃, OCF₃, OCF₂H, CN, SR², (CH₂)$_d$C(O)OR², C(O)N(R²)₂, (CH₂)$_d$OR², HNC(O)R², HN—C(O)OR², (CH₂)$_d$N(R²)₂, SO₂N(R²)₂, OP(O)(OR²)₂, OC(O)OR², OCH₂O;

b is 0 or an integer of from 1 to 2;

a is 0 or an integer of from 1 to 3;

c is an integer of from 1 to 2;

d is 0 or an integer of from 1 to 5 and further provided said alkyl or phenyl radicals may be substituted with one or two halo, hydroxy, lower alkyloxy, or lower alkyl amino radicals; and pharmaceutically acceptable salts thereof.

2. The compound of claim 1 wherein c is 1.
3. The compound of claim 2 wherein R² is H.
4. The compound of claim 3 wherein b is 0.
5. The compound of claim 3 wherein R¹ is selected from the group consisting of CH₃, F and Cl.
6. The compound of claim 3 wherein a is 0.
7. The compound of claim 3 wherein R is selected from the group consisting of NHCOR⁷ and N(R⁷)₂ wherein R⁷ is selected from the group consisting of hydrogen, C₁ to C₄ alkyl and phenyl, wherein said alkyl or phenyl may be substituted with hydroxy, methylol or amino substituents.
8. The compound of claim 6 wherein R⁷ is selected from the group consisting of hydrogen, methyl, ethyl, hydroxypropyl and aminomethylolphenyl.
9. The compound of claim 1 wherein said compound is selected from the group consisting of 3-(3H-isobenzofuran-1-ylidene)-1,3-dihydro-indol-2-one,
5-Chloro-3-(3H-isobenzofuran-1-ylidene)-1,3-dihydro-indol-2-one,
3-(3H-Isobenzofuran-1-ylidene)-4-methyl-1,3-dihydro-indol-2-one,
5-Fluoro-3-(3H-isobenzofuran-1-ylidene)-1,3-dihydro-indol-2-one,
3-(6-Amino-3H-isobenzofuran-1-ylidene)-1,3-dihydro-indol-2-one,
N-[3-(2-Oxo-1,2-dihydro-indol-3-ylidene)-1,3-dihydro-isobenzofuran-5-yl]-acetamide,
N-[3-(2-Oxo-1,2-dihydro-indol-3-ylidene)-1,3-dihydro-isobenzofuran-5-yl]-butyramide,
Cyclopropanecarboxylic acid [3-(2-oxo-1,2-dihydro-indol-3-ylidene)-1,3-dihydro-isobenzofuran-5-yl]-amide,
4-Chloro-N-[3-(2-oxo-1,2-dihydro-indol-3-ylidene)-1,3-dihydro-isobenzofuran-5-yl]-butyramide,
2-(4-Methoxy-phenyl)-N-[3-(2-oxo-1,2-dihydro-indol-3-ylidene)-1,3-dihydro-isobenzofuran-5-yl]-acetamide,
3-(6-Ethylamino-3H-isobenzofuran-1-ylidene)-1,3-dihydro-indol-2-one,
3-(5-Amino-3H-isobenzofuran-1-ylidene)-1,3-dihydro-indol-2-one,
5-Amino-2-hydroxymethyl-N-[3-(2-oxo-1,2-dihydro-indol-3-ylidene)-1,3-dihydro-isobenzofuran-5-yl]-benzamide,
3-[6-(3-Hydroxy-propylamino)-3H-isobenzofuran-1-ylidene]-1,3-dihydro-indol-2-one,
3-(5-Ethylamino-3H-isobenzofuran-1-ylidene)-1,3-dihydro-indol-2-one,
3-(6-Amino-3H-isobenzofuran-1-ylidene)-5-chloro-1,3-dihydro-indol-2-one,
3-(5-Amino-3H-isobenzofuran-1-ylidene)-5-chloro-1,3-dihydro-indol-2-one,
N-[1-(2-Oxo-1,2-dihydro-indol-3-ylidene)-1,3-dihydro-isobenzofuran-5-yl]-acetamide,
N-[1-(5-Chloro-2-oxo-1,2-dihydro-indol-3-ylidene)-1,3-dihydro-isobenzofuran-5-yl]-acetamide,
N-[3-(5-Chloro-2-oxo-1,2-dihydro-indol-3-ylidene)-1,3-dihydro-isobenzofuran-5-yl]-acetamide,
3-(6-Dimethylamino-3H-isobenzofuran-1-ylidene)-1,3-dihydro-indol-2-one,
3-(6-Methylamino-3H-isobenzofuran1-ylidene)-1,3-dihydro-indol-2-one,
3-(5-Dimethylamino-3H-isobenzofuran-1-ylidene)-1,3-dihydro-indol-2-one,
3-(5-Methylamino-3H-isobenzofuran-1-ylidene)-1,3-dihydro-indol-2-one,
4-Chloro-N-[3-(2-oxo-1,2-dihydro-indol-3-ylidene)-1,3-dihydro-isobenzofuran-5-yl]-propionamide and
3-(6-Ethylamino-3H-isobenzofuran-1-ylidene)-1,3-dihydro-indol-2-one.

10. The compound of claim 9 wherein said compound is selected from the group consisting of 3-(3H-isobenzofuran-1ylidene)-1,3-dihydro-indol-2-one,
5-Chloro-3-(3H-isobenzofuran-1-ylidene)-1,3-dihydro-indol-2-one,
3-(3H-Isobenzofuran-1-ylidene)-4-methyl-1,3-dihydro-indol-2-one,
5-Fluoro-3-(3H-isobenzofuran-1-ylidene)-1,3-dihydro-indol-2-one,
3-(6-Amino-3H-isobenzofuran-1-ylidene)-1,3-dihydro-indol-2-one,
N-[3-(2-Oxo-1,2-dihydro-indol-3-ylidene)-1,3-dihydro-isobenzofuran-5-yl]-acetamide,
3-(6-Ethylamino-3H-isobenzofuran-1-ylidene)-1,3-dihydro-indol-2-one,
3-(5-Amino-3H-isobenzofuran-1-ylidene)-1,3-dihydro-indol-2-one,
5-Amino-2-hydroxymethyl-N-[3-(2-oxo-1,2-dihydro-indol-3-ylidene)-1,3-dihydro-isobenzofuran-5-yl]-benzamide,
3-[6-(3-Hydroxy-propylamino)-3H-isobenzofuran-1-ylidene]-1,3-dihydro-indol-2-one,
3-(6-Amino-3H-isobenzofuran-1-ylidene)-5-chloro-1,3-dihydro-indol-2-one,
3-(5-Amino-3H-isobenzofuran-1-ylidene)-5-chloro-1,3-dihydro-indol-2-one,
N-[1-(2-Oxo-1,2-dihydro-indol-3-ylidene)-1,3-dihydro-isobenzofuran-5-yl]-acetamide,
N-[1-(5-Chloro-2-oxo-1,2-dihydro-indol-3-ylidene)-1,3-dihydro-isobenzofuran-5-yl]-acetamide and
N-[3-(5-Chloro-2-oxo-1,2-dihydro-indol-3-ylidene)-1,3-dihydro-isobenzofuran-5-yl]-acetamide.

11. A method for treating diseases related to unregulated tyrosine kinase signal transduction, the method comprising the step of administering to a subject in need thereof a therapeutically effective amount of a compound represented by the general formula I:

19

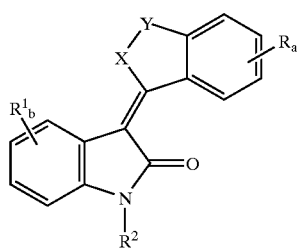

wherein
X is O;
Y is $[C(R^2)_2]_c$;
$R^1$ is selected from the group consisting of halogen, $C_1$ to $C_8$ alkyl; $CF_3$, $OCF_3$, $OCF_2H$, CN, $SR^2$, $(CH_2)_bC(O)OR^2$, $C(O)N(R^2)_2$, $(CH_2)_bOR^2$, $HNC(O)R^2$, HN—C(O)OR$^2$, $(CH_2)_bN(R^2)_2$, $SO_2N(R^2)_2$, $OP(O)(OR^2)_2$, $OC(O)OR^2$, $OCH_2O$, $N(R^2)(CH_2)_dN(R^2)_2$ and $O(CH_2)_dN(R^2)_2$;
$R^2$ is selected from the group consisting of hydrogen and $C_1$ to $C_8$ alkyl and phenyl;
R is selected from the group consisting of halogen, $C_1$ to $C_8$ alkyl, $CF_3$, $OCF_3$, $OCF_2H$, CN, $SR^2$, $(CH_2)_dC(O)OR^2$, $C(O)N(R^2)_2$, $(CH_2)_dOR^2$, $HNC(O)R^2$, HN—C(O)OR$^2$, $(CH_2)_dN(R^2)_2$, $SO_2N(R^2)_2$, $OP(O)(OR^2)_2$, $OC(O)OR^2$, $OCH_2O$;
b is 0 or an integer of from 1 to 2;
a is 0 or an integer of from 1 to 3;
c is an integer of from 1 to 2; d is 0 or an integer of from 1 to 5 and further provided said alkyl or phenyl radicals may be substituted with one or two halo, hydroxy, lower alkyloxy, or lower alkyl amino radicals; and pharmaceutically acceptable salts thereof.

12. The method of claim 11 wherein said disease is selected from the group consisting of cancer, blood vessel proliferative disorders, fibrotic disorders, mesangial cell proliferative disorders and metabolic diseases.

13. The method of claim 11 wherein the blood vessel proliferative disorder is selected from the group consisting of diabetic retinopathy, age-related macular degeneration, retinopathy of prematurity, arthritis and restenosis.

14. The method of claim 11 wherein the fibrotic disorder is selected from the group consisting of hepatic cirrhosis, atherosclerosis and surgical adhesions.

15. The method of claim 11 wherein the mesangial cell proliferative disorder is selected from the group consisting of glomerulonephritis, diabetic nephropathy, malignant nephrosclerosis, thrombotic microangiopathy syndromes, transplant rejection and glomerulopathies.

16. The method of claim 11 wherein the metabolic disorder is selected from the group consisting of psoriasis, diabetes mellitus, wound healing, inflammation and neurodegenerative diseases.

20

17. A compound represented by the general formula II

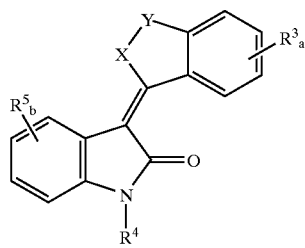

wherein X is O; Y is $[C(R^4)_2]_c$; $R^5$ is selected from the group consisting of halogen, nitro, hydroxy, hydrocarbyl, substituted hydrocarbyl, amide, thioamide, amine, thioether and sulfonyl; $R^3$ is selected from the group consisting of halogen, nitro, hydroxy, hydrocarbyl, substituted hydrocarbyl, amide, thioamide, amine, thioether and sulfonyl and phosphonic acid; $R^4$ is selected from the group consisting of hydrogen, hydrocarbyl and substituted hydrocarbyl; c is an integer of from 1 to 2; b is 0 or an integer from 1 to 2; a is 0 or an integer of from 1 to 3 and pharmaceutically acceptable salts thereof.

18. A method for treating diseases related to unregulated tyrosine kinase signal transduction, the method comprising the step of administering to a subject in need thereof a therapeutically effective amount of a compound represented by the general formula II:

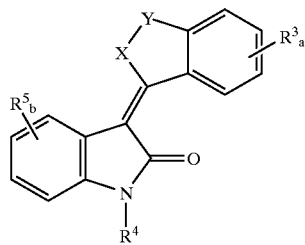

wherein X is O; Y is $[C(R^4)_2]_c$; $R^5$ is selected from the group consisting of halogen, nitro, hydroxy, hydrocarbyl, substituted hydrocarbyl, amide, thioamide, amine, thioether and sulfonyl; $R^3$ is selected from the group consisting of halogen, nitro, hydroxy, hydrocarbyl, substituted hydrocarbyl, amide, thioamide, amine, thioether and sulfonyl and phosphonic acid; $R^4$ is selected from the group consisting of hydrogen, hydrocarbyl and substituted hydrocarbyl; c is an integer of from 1 to 2; b is 0 or an integer from 1 to 2; a is 0 or an integer of from 1 to 3 and pharmaceutically acceptable salts thereof.

* * * * *

UNITED STATES PATENT AND TRADEMARK OFFICE
CERTIFICATE OF CORRECTION

PATENT NO. : 6,541,504 B1
DATED : April 1, 2003
INVENTOR(S) : Andrews et al.

It is certified that error appears in the above-identified patent and that said Letters Patent is hereby corrected as shown below:

Column 1,
Line 37, delete "RTKS" and insert in place thereof -- RTKs --

Column 12,
Line 25, delete "6Ethylamino" and insert in place thereof -- 6-Ethylamino --

Column 13,
Line 11, delete "$Cl_3/$" and insert in place thereof -- $Cl_3/$ --

Signed and Sealed this

Seventeenth Day of June, 2003

JAMES E. ROGAN
*Director of the United States Patent and Trademark Office*